United States Patent
Kaminski

(10) Patent No.: US 7,820,795 B2
(45) Date of Patent: Oct. 26, 2010

(54) LACTOBACILLUS FERMENTUM N-DESOXYRIBOSYL TRANSFERASES AND THE USE THEREOF FOR ENZYMATIC SYNTHESIS OF 2', 3'—DIDESOXYNUCLEOSIDES AND 2',3'-DIDEHYDRO-2',3'- DIDESOXYNUCLEOSIDES

(75) Inventor: Pierre-Alexandre Kaminski, Paris (FR)

(73) Assignee: Institut Pasteur, Paris (FR)

( * ) Notice: Subject to any disclaimer, the term of this patent is extended or adjusted under 35 U.S.C. 154(b) by 844 days.

(21) Appl. No.: 10/594,766

(22) PCT Filed: Mar. 29, 2005

(86) PCT No.: PCT/FR2005/000743

§ 371 (c)(1),
(2), (4) Date: Sep. 29, 2006

(87) PCT Pub. No.: WO2005/095596

PCT Pub. Date: Oct. 13, 2005

(65) Prior Publication Data

US 2008/0064646 A1  Mar. 13, 2008

(30) Foreign Application Priority Data

Mar. 30, 2004  (FR) .................. 04 03319

(51) Int. Cl.
*A23J 1/18* (2006.01)
*C12Q 1/48* (2006.01)
*C12N 15/63* (2006.01)
*C12N 15/85* (2006.01)
*C12N 15/11* (2006.01)

(52) U.S. Cl. .................. 530/371; 435/15; 435/320.1; 435/325; 536/23.1

(58) Field of Classification Search .................. None
See application file for complete search history.

(56) References Cited

U.S. PATENT DOCUMENTS 7,381,555 B2 * 6/2008 Kaminski et al. .......... 435/193

FOREIGN PATENT DOCUMENTS

| WO | WO03/025163 | * | 9/2002 |
| WO | 03 025163 | | 3/2003 |
| WO | 2004 087918 | | 10/2004 |

OTHER PUBLICATIONS

Sutherland, John D. et at.," Directed Evolution of Novel Biosynthetic Pathways: Growuth of an *Escherichia coli* Proline Auxotroph on Delta-1-Pyrroline-2-Carboxylic Acid", Bioorganic and Medicinal Chemistry Letters, vol. 3, No. 6, pp. 1185-1188, 1993.
Chartrain, Michel et al.," Metabolic Engineering and Directed Evolution for the Production of Pharmaceuticals", Biochemical Engineering, vol. 11, No. 2, pp. 209-214, 2000.
Bornscheuer, U. T.," Directed Evolution of Enzymes for Biocatalytic Applications", Harwood Academic Publishers Imprint, vol. 19, No. 2, pp. 85-97, 2001.

* cited by examiner

*Primary Examiner*—Michele K Joike
(74) *Attorney, Agent, or Firm*—Oblon, Spivak, McClelland, Maier & Neustadt, L.L.P.

(57) ABSTRACT

N-deoxyribosyl transferases of *Lactobacillus fermentum* and their analogues, as well their use for the enzymatic synthesis of 2',3'-dideoxynucleosides and 2',3'-didehydro-2',3'-dideoxynucleosides. These transferases and their analogues include a N-deoxyribosyl transferase protein (DTP) that has at least 70%-95% identity with the polypeptide of SEQ ID NO: 2 or SEQ ID NO: 4, that retains residues Y13, D77, D97, E103, and M312 which respectively correspond to positions 13, 77, 97, 103, and 132 of SEQ ID NO: 2; and that has threonine at a position corresponding to position 15 of SEQ ID NO: 2 or SEQ ID NO: 4. Polynucleotides, vectors and host cells encoding these N-deoxyribosyl transferases and their analogues.

22 Claims, 4 Drawing Sheets

Figure 1a: Diagram of the *"de novo"* route of UTP and CTP in *E. coli*
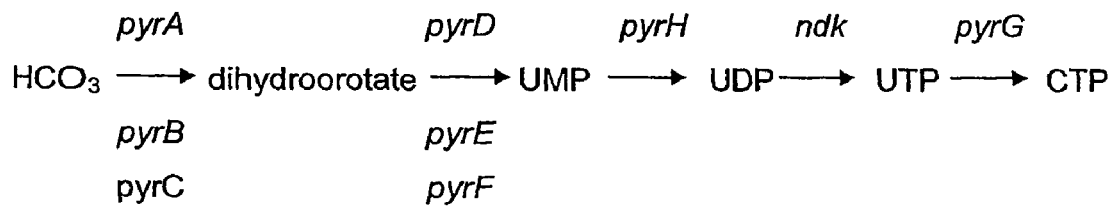

Figure 1b: Recycling route of the pyrimidines in E. coli
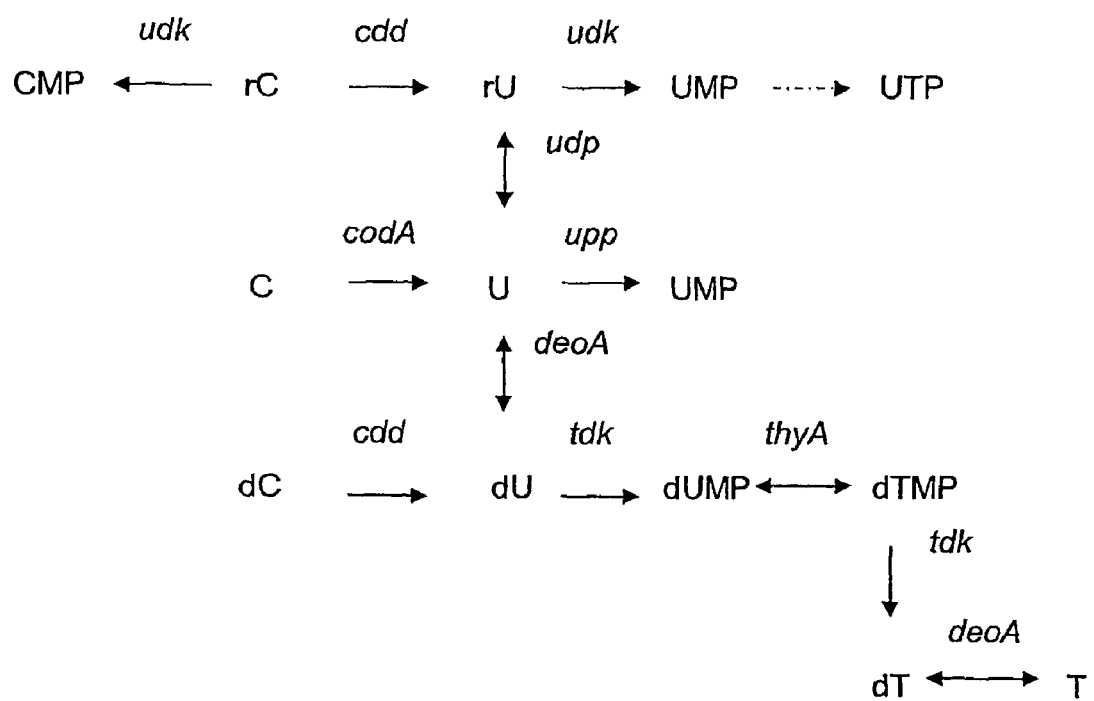

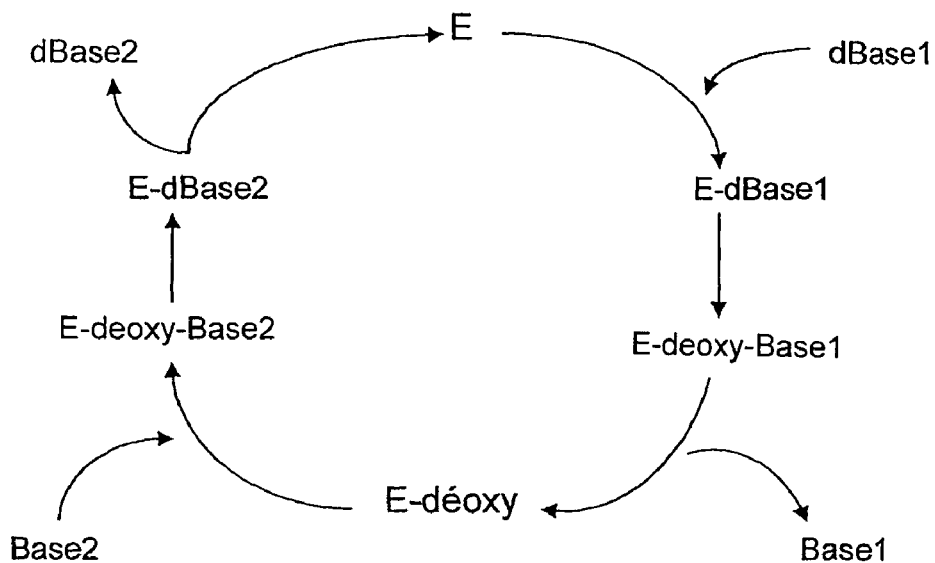
*E-deoxy = enzyme-deoxyribose complex with the form]
(E = active site of the enzyme)
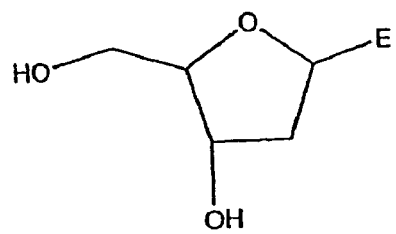
* dBase = deoxyribonucleotide
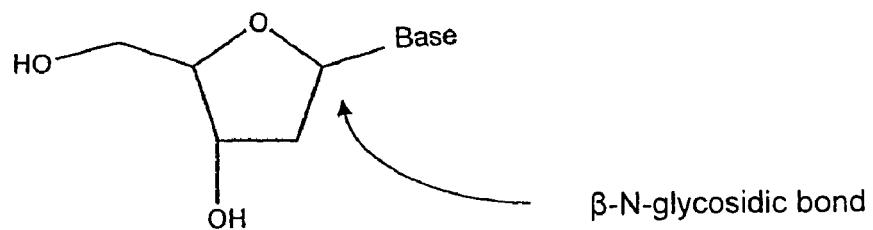
FIGURE 2

CLUSTAL W (1.8) multiple sequence alignment

```
                                     13
NTDLh            MNKKKTLYFGAGWFNEKQNKA--YKEAMAALKENPTVDLENSYVPLENQYKGIRI
NTDLa            MMAKTKTLYFGAGWFNEKQNKA--YKAAMEALKQNPTVDLENSYVPLENQYKDIRV
NTDLj                  MAGWFTETQNKA--YKDAMSALNANPTIDLENSYVPLQNQYKDIRV
NTDLl            MPKKTIYFGAGWFTDRQNKA--YKEAMEALKENPTIDLENSYVPLDNQYKGIRV
NTDLf            LKNTDPVANTKIYLATSFFNEEQRAR--IPQALAQLEANPTVGVVH--QPFDFQYKDARV
PTDLh            MKAVVPTGKIYLGSPFYSDAQRER--AAKAKELLAKN--LSIAHVFFPFDDGFTDPDE
NTDLmATCC8293           MSQIYLAGPFFSDEQIDR--VKRIEAALDSN---------PTVTDYYSPRK
ProMar             MTRKIIYLASPYGFSKQCKKNLLPEFIAALEDLG-----------AEVWEPFSR 77                 97   103
NTDLh            DEHPEYLH-NIEWASATYHNDLVGIKTSDVMLGVYLP--EEEDVGLGMELGYALSQGKYI
NTDLa            DEHPEYLH-DIEWASATYHNDLIGIKSSDIMLGVYLP--EEEDVGLGMELGYALSQGKYI
NTDLj            DEHPEYLH-DKEWAQATYNGDLVGIKTSDVMLGVYVP--KEEDVGLGMELGYAMSQGKYV
NTDLl            DEHPEYLH-DKVWATATYNNDLNGIKTNDIMLGVYIP--DEEDVGLGMELGYALSQGKYV
NTDLf            DSDPAGVFGSLEWQIATYNNDLNAVGTSDVCVALYDM--DQIDEGICMEIGMFVALHKPI
PTDLh            KNPEIGGIRSMVWRDATYQNDLTGISNATCGVFLYDM--DQLDDGSAFEIGFMRAMHKPV
NTDLmATCC8293    HQKTENPEFTSPWAAEVFQRDIKNVTDADIILSIIDYRDNDADSGTAFEQGMAWVQKKPI
ProMar           NAQYENLQ--PGWAHDIALADLRDVRNSDGILAVVNG--TPPDEGVMIELGAAIALGKPT

132
NTDLh            LLVIP------DED-YGKPINLMSWGVCDNAIK----ISELKDFDFNKPRYN-FYDGAVY
NTDLa            LLVIP------DED-YGKPINLMSWGVCDNAIK----ISELKDFDFNKPRFN-FYDGAVY
NTDLj            LLVIP------DEL-YGESINLMSWGVADNVIK----MSELATFDFNRPRYN-FYDGAVY
NTDLl            LLVIP------DED-YGKPINLMSWGVSDNVIK----MSQLKDFNFNKPRFD-FYEGAVY
NTDLf            VLLPFTKK---DKSAYEA--NLMLARGVTTWLEPN-DFSPLKDFNFNHPMAQPFPPPKVF
PTDLh            ILVPFTEH---PEKEKKM--NLMIAQGVTTIIDGNTEFEKLADYNFNECPFNPVRGYGIY
NTDLmATCC8293    IVFN--------ELKFPV--NLMLSESLTAYITN---SDDIATYDFDQTPKLPFTG-ELF
ProMar           FLFRDDFRRCSDSEEYPL--NLMLFAGLPSIGWNDYFYTSIEELSDPKKSLAIWLKD---
```

Figure 3

LACTOBACILLUS FERMENTUM N-DESOXYRIBOSYL TRANSFERASES AND THE USE THEREOF FOR ENZYMATIC SYNTHESIS OF 2', 3'—DIDESOXYNUCLEOSIDES AND 2',3'-DIDEHYDRO-2',3'- DIDESOXYNUCLEOSIDES

The present invention relates to novel N-deoxyribosyl transferases of *Lactobacillus fermentum* and their use for the enzymatic synthesis of 2',3'-dideoxynucleosides and 2',3'-didehydro-2',3'-dideoxynucleosides.

Nucleoside analogues are very widely used in antiviral therapies or in anti-cancer chemotherapy. For example there can be mentioned ddI (didanosine), ddC (zalcitabine) and d4T (stavudine) or AZT (zidovudine) in anti-HIV therapy, ACV (acyclovir) in the treatment of herpes or also GCV (ganciclovir) used in anti-tumor therapy in combination with herpes thymidine kinase.

The dideoxynucleosides such as ddI and ddC and their derivatives are the most effective inhibitors known at present used in therapy against the HIV virus.

The chemical synthesis of these compounds requires several stages of protections, deprotections and purifications. It would therefore be desirable to be able to simplify the procedures for synthesis of this type of compounds by developing selective enzymatic and highly specific methods.

The N-deoxyribosyl transferases produced by bacteria of the *Lactobacillus* genus are enzymes which catalyze the transfer of deoxyribose between two puric or pyrimidic bases. They are also capable in general of transferring 2',3'-dideoxyribose between these same bases (Carson and Wasson, 1988). Thus, it has been possible to synthesize several pyrazolo (3,4-d) pyrimidines and triazolo (4,5-d) pyrimidines derived from 2',3'-dideoxycytidine and the corresponding base from enzymes of *Lactobacillus leichmannii* and *Lactobacillus helveticus* (Fischer et al., 1990). The 2',3'-dideoxyribose transfer reaction is however clearly less effective than that carried out with 2'-deoxyribose.

It has been found within the framework of the present invention that the introduction of mutations into N-deoxyribosyl transferase of *Lactobacillus fermentum* (*L. fermentum*), followed by a confrontation with an analogue of the natural substrate within selective screening made it possible to obtain a mutated protein having a strong activity on the novel substrate. By repeating these operations, it appeared possible to obtain enzymes having an activity on substrates more and more distant from the initial natural substrate.

It was after a stage of random mutagenesis in an ntd gene of *L. fermentum*, followed by a selection stage using a functional genetic screen that it has been possible to isolate mutants having a more significant specific activity, in particular for the transfer of 2',3'-dideoxyribose.

This method for selecting more active modified enzymes more particularly involves as genetic screen the *E. coli* strain PAK 9 (deposited at the CNCM on 27 Jun. 2002 under accession number 1-2902), which is of genotype ΔpyrC::Gm, ΔcodA::Km, cdd::Tn10.

This strain makes it possible to select the production of uracil as it is deleted for the pyrc gene which controls the conversion of carbamyl aspartate to dihydroorotate as well as for the codA and cdd genes which control respectively the deamination of cytosine and (deoxy)cytidine. It therefore has a requirement for uracil (u) which can only be satisfied by the introduction of uridine (R-U), deoxyuracil (dR-U) or dideoxyuracil (ddR-U). However the use of dideoxyuracil (ddR-U) can be selected from the strain PAK9 only if a variant of N-deoxyribosyl transferase is capable of producing one of the following two reactions:

$$ddR\text{-}U \rightarrow U + ddR, \qquad\qquad i$$

$$ddR\text{-}U \rightleftharpoons C = ddR\text{-}C + U \qquad\qquad ii$$

The transforming clones of PAK 9 expressing a randomly mutated ntd gene of *L. fermentum*, were thus selected in glucose mineral medium to which dideoxyuracil (ddR-U) and cytosine (C) have been added. Several transforming clones were obtained and are capable of carrying out the exchange $$ddR\text{-}Pyr + Pur \rightleftharpoons ddR\text{-}Pur + Pyr$$

as well as $$dR\text{-}Pyr + Pur \rightleftharpoons dR\text{-}Pur + Pyr.$$

The nucleotide sequences of the different variants of ntd of *L. fermentum* can differ from the wild-type gene only by a single mutation. Their enzymatic activities were evaluated from crude extracts or purified proteins. The specific activity of NTD* can be 10 times less than that of NTD for the transfer of deoxyribose but can be 7 times more for the transfer of dideoxyribose.

The selected enzyme is used in the enzymatic synthesis of 2',3'-dideoxynucleosides and 2',3'-didehydro-2',3'-dideoxynucleosides of natural or modified bases (5-halogenopyrimidines), comprising or not comprising radioelements. The method can be extended to the selection of variants capable of transferring derivatives of 2'-deoxyribose or 2',3'-dideoxyribose between bases (such as 3'-amino-2',3'dideoxyribose or 3'-azido-2',3'-dideoxyribose).

Moreover, in the method according to the invention, cells in which a metabolic pathway has been inactivated can be used. The selective screening consists of making up for this deficiency by producing the product P for which the cells are auxotrophic from an analogue of the natural substrate of the protein X.

Alternatively, it is possible to evolve a protein X by complementation of a related protein Y, X and Y both belonging to the same EC enzyme nomenclature class or to adjacent classes.

DESCRIPTION

Thus, the present invention generally relates to a method of in vitro and in vivo artificial evolution of an X protein encoded by an ntd gene of *L. fermentum*, said method making it possible to evolve said X protein in vivo by complementation either of a related protein, or by complementation of an inactivated metabolic route.

Such a method makes it possible to evolve an X protein encoded by an ntd gene of *L. fermentum* so as to modify its characteristics by the following stages:

a) obtaining mutants of the ntd gene of *L. fermentum* by random mutagenesis;

b) transformation of cells comprising a [P−] phenotype with vectors comprising the mutated nucleic acid obtained in stage a) coding for the X* proteins thus modified, P− meaning that said cells are auxotrophic for the substance P, P being the product of the action of X on its natural substrate S;

c) culture of said cells in a medium comprising a substrate S*, S* being an analogue of the natural substrate S of said X protein;

d) selection of the cells [P–:: X*] which have survived stage c) in which the X* proteins are capable of carrying out the biosynthesis of the product P from the substrate S*.

The mutant X* protein obtained is a protein possessing an activity similar to that of natural N-deoxyribosyl transferase X. X* thus belongs to the same enzyme classes or to enzyme classes adjacent to N-deoxyribosyl transferases having at least the first three figures of the international 4-figure EC nomenclature classes. In order to pass from one class to another, the abovementioned method can be repeated with, at each passage, the addition of an additional modification to the substrate analogue designated by S*.

By "substrate analogue", is meant the natural substrate S of the natural X protein comprising a modification or alteration. By "modification of this substrate", is meant the addition or deletion of at least one atom, group or substituent, the modification of the spatial conformation of the substrate (isomeric, enantiomeric, diasteroisomeric). This modification can be minimal or significant from the structural point of view. In the case where it is sought to substantially modify the activity of the protein (or enzyme), the method can be repeated, further modifying the substrate S* at each new selection cycle. Little by little, the protein accumulates mutations which are responsible for the modification of its activity.

In this process, the cells used in stage b) are obtained by inactivation of at least one gene involved in the natural metabolic pathway leading to the product P.

Thus, the X* protein obtained makes up for the deficiency of the natural metabolic pathway leading to the product P in a medium provided with the substrate S*.

By "complement", is meant the deletion of the auxotrophic phenotype resulting from the inactivation of the gene or the metabolic route.

Alternatively, the cells can be cells in which the gene coding for a protein related to X has been inactivated beforehand.

By "inactivation", is meant a deletion in whole or in part, an insertion, or a mutation rendering the gene inoperative. The inactivation can also consist of a modification leading to a phenotype of the Ts (temperature-sensitive) type. In this case, the cells are cultured at temperatures not permissible during the selection phase (stages c) and d)).

Preferably, the related protein Y previously mentioned possesses at least the first three figures (2.4.2) of the international 4-figure EC nomenclature (Table 1), more particularly forms part of class EC 2.4.2.6 (N-deoxyribosyl transferases).

TABLE 1

| EC Number | Name according to the international nomenclature |
| --- | --- |
| 2.4.2.5 | Nucleoside ribosyl transferase. |
| 2.4.2.6 | Nucleoside deoxyribosyl transferase |
| 2.4.2.7 | Adenine phosphoribosyl transferase |
| 2.4.2.8 | Hypoxanthine phosphoribosyl transferase. |
| 2.4.2.9 | Uracil phosphoribosyl transferase. |
| 2.4.2.10 | Orotate phosphoribosyl transferase. |
| 2.4.2.11 | Nicotinate phosphoribosyl transferase. |
| 2.4.2.12 | Nicotinamide phosphoribosyl transferase. |
| 2.4.2.14 | Amidophosphoribosyl transferase. |
| 2.4.2.17 | ATP phosphoribosyl transferase. |
| 2.4.2.18 | Anthranilate phosphoribosyl transferase. |
| 2.4.2.20 | Dioxotetrahydropyrimidine phosphoribosyl transferase. |
| 2.4.2.21 | Nicotinate-Nucleotide-dimethylbenzimidazole phosphoribosyl transferase. |
| 2.4.2.22 | Xanthine-guanine phosphoribosyl transferase. |
| 2.4.2.29 | Queuine tRNA-ribosyl transferase. |
| 2.4.2.30 | NAD (+) ADP-ribosyl transferase. |

TABLE 1-continued

| EC Number | Name according to the international nomenclature |
| --- | --- |
| 2.4.2.31 | NAD (P) (+)-arginine ADP-ribosyl transferase. |
| 2.4.2.36 | NAD (+)-diphthamide ADP-ribosyl transferase. |
| 2.4.2.37 | NAD (+)-dinitrogeN-reductase ADP-D-ribosyl transferase. |

Advantageously, the activity of N-deoxyribosyl transferase X on the substrate S is at least 2, 5, 10, 25, 50, 100 or 1000 times greater than its activity on the substrate S*. In parallel, the activity of the X* protein on the substrate S* is at least 5, 10, 25, 50, 100 or 1000 times greater than its activity on the substrate S.

The random mutagenesis of stage a) can be carried out either by variation of the manganese concentration during the PCR reaction, or by use of promutagenic nucleotide analogues or also by the utilization of primers comprising a random sequence. Different techniques are described in the documents U.S. Pat. No. 6,323,030 (Methods for generating polynucleotides having desired characteristics by iterative selection and recombination), U.S. Pat. No. 6,177,263 (Recombination of polynucleotide sequences using random or defined primers), WO 01/66798 (Random truncation and amplification of nucleic acid), and EP1205547 (DNA mutagenesis by random fragmentation and reassembly).

The cells used within the framework of the invention are prokaryotic or eukaryotic cells, preferably *E. coli*.

In a particular embodiment, the invention relates to a method as described above for evolving an N-deoxyribosyl transferase (DTP) so as to obtain an N-dideoxyribosyl transferase, characterized in that it comprises the following stages:

a) obtaining DTP* mutants of the sequence of the ntd gene of *L. fermentum* coding for an N-deoxyribosyl transferase (DTP) by random mutagenesis;

b) transformation of cells comprising a phenotype [N–] with vectors comprising the mutated nucleic acids obtained in Stage a) coding for the DTP* proteins, N– meaning that said cells are auxotrophic for at least one nucleoside, said nucleoside being the product of the action of DTP on its natural substrate dR-N;

c) culture of said cells in a medium comprising a ddR-N substrate;

d) selection of the [N–:: DTP*] cells which have survived Stage c) in which the DTP* proteins are capable of carrying out the transfer of the dideoxyribose (ddR) from a dideoxyribonucleoside to another nucleoside leading to the production of the N nucleoside necessary for the survival of the cells.

By "N nucleoside", is meant a natural nucleoside, i.e. molecules constituted by a sugar linked to a heterocyclic base by an N-glycosidic bond, the bases being pyrimidines (thymine, uracil, cytosine) or purines (adenine, guanine from the usual bases). By "N–" is meant an [A-, T-, G-, C-, U- or I-]phenotype.

The NTD* enzyme obtained can be capable of recognizing and transferring a deoxyribose analogue such as dideoxyribose, but also of acting on nucleoside analogues. Thus, the analogue of substrate S* used can be an analogue of deoxyribonucleoside or didehydrodideoxyribonucleosides comprising at least one chemical modification on the base and/or on the ribose.

More particularly, the coding sequence (ntd) of N-deoxyribosyl transferase (DTP) of *L. fermentum* corresponds to SEQ ID No. 1.

In this process, in stage b) bacteria of the genotypes ΔpyrC, ΔcodA, Δcdd deficient in the metabolic pathway leading to uracil can be used. The *E. coli* strain PAK 9 deposited at the CNCM on 27 Jun. 2002 under No. 1-2902, is particularly suited to this use.

Advantageously, the present invention aims, starting with the method described above, to obtain from the protein X encoded by ntd of *L. fermentum*, a mutated protein having an N-dideoxyribosyl transferase activity and/or an activity on analogues of deoxy or dideoxyribonucleoside comprising a modified base. The sequence of the thus mutated protein in general has a percentage identity greater than or equal to 70%, in particular 80%, preferentially greater than or equal to 90%, and more preferentially greater than or equal to 95% with the sequence SEQ ID No. 2. It is moreover important that certain residues of the sequence ID No. 2 be preserved so that said mutated protein has an optimum enzymatic activity. This is the case in particular with the residues Y13 (tyrosine in position 13), D77 (aspartic acid in position 77), D97 (aspartic acid in position 97), E103 (glutamic acid in position 103), M132 (methionine in position 132). Thus, certain variants can have a percentage identity with the sequence ID No. 2 comprised between 70% and 80% in the regions which are situated outside the catalytic site of the enzyme constituted by said residues. These variants then have a sequence at least 70% identical to SEQ ID No. 2, in which the residues Y13, D77, D97, E103, M132 are preserved, preferably at least 80%.

The invention thus also consists of a protein having an activity on of deoxy- or dideoxyribonucleoside analogues, having a percentage identity with SEQ ID No. 4 equal to or greater than 70%, preferably 75%, and in order of preference, respectively 80%, 85%, 90%, 95% and 98%, and comprising a threonine residue corresponding to the mutation point A15T of SEQ ID No. 4. The correspondence between the threonine residue and the mutation point A15T of SEQ ID No. 4 is in general established by alignment of the sequence of said protein with SEQ ID No. 4 as represented in FIG. 3 of the present Application.

Such a protein comprises in general, moreover, the residues corresponding to Y13, D77, D97, E103 and M132 of SEQ ID No. 4, which are necessary for good catalytic activity.

Preferably, a protein according to the invention has an N-dideoxyribosyl transferase activity, which in general manifests itself by a deoxyribose and dideoxyribose and/or didehydroribose transfer activity.

A protein as defined above in general has a catalytic activity on d4T and ddT preferably at least 50% greater than that of the native N-deoxyribosyl transferase protein of *L. fermentum* represented by SEQ ID No. 2.

This catalytic activity manifests itself in particular by a catalytic effectiveness on d4T and ddT at least 5 times, preferably at least 7 times, greater than that of the native N-deoxyribosyl transferase protein of *L. fermentum* represented by SEQ ID No. 2. The catalytic effectiveness on ddT is in general 10 times, preferably 20 times and more preferentially 50 times greater than that of the native N-deoxyribosyl transferase protein of *L. fermentum* represented by SEQ ID No. 2.

By catalytic effectiveness is meant the result of the quotient Kcat/Km, which reflects the number of times that a enzyme carries out a reaction (transformation of its substrate), compared with the number of times that said enzyme forms a complex with its substrate. Thus the more effective an enzyme is, the higher will be the value of its Kcat/Km quotient.

A particularly preferred mutated protein of the invention comprises the mutation A15T, such as for example the protein of sequence SEQ ID No. 4.

The invention also relates to a nucleic acid comprising a mutated ntd (NTD*) sequence coding for a mutated protein as defined previously and having a N-deoxyribosyl transferase activity and/or an activity on analogues of deoxy or dideoxyribonucleoside comprising a mutated modified base. A preferred nucleic acid of the invention comprises the sequence SEQ ID No.3, which codes for the protein corresponding to SEQ ID No. 4.

The invention also relates to an expression vector comprising a nucleic acid as defined above, in particular the sequence SEQ ID No. 3. This sequence can be fused to a promoter effective for the expression of all or part of said sequence in the eukaryotic and/or prokaryotic cells. The vector can be a plasmid capable of transforming and being maintained in *E. coli*. The vector can be maintained in the bacterium in a stable or transitory manner.

The invention also relates to a host cell comprising a vector as described previously, such as the strain of *E. coli* deposited at the CNCM on 22 Mar. 2004 under accession number 1-3192 which comprises the vector pETLFA15T described below.

In another aspect, the invention relates to the use of an N-dideoxyribosyl transferase described above for the transfer of a dideoxyribose (ddR) from a dideoxyribonucleoside to another nucleoside, in particular in order to obtain the synthesis of 2',3'-dideoxynucleosides and 2',3'-didehydro-2',3'-dideoxynucleosides.

This enzyme obtained from the method according to the invention is particularly useful for the preparation of nucleoside analogues possessing anti-tumor properties, in particular ddI or ddC.

Thus, the invention also relates to a method for the preparation of compounds comprising a stage consisting of utilizing a mutated protein defined above.

This method is particularly advantageous for the preparation of nucleoside or nucleotide analogues useful for the treatment of cancer or infectious diseases, in particular dideoxyribonucleosides, in particular ddC or ddI and 2',3'-didehydro-2',3'-dideoxynucleosides.

Reference will be made to the legends of the figures below in the remainder of the description.

LEGENDS

FIG. 1: Biosynthesis routes

FIG. 1*a*) the "de novo" synthesis of DNA from simple precursors.

The abbreviations used are as follows:
ndk: nucleoside diphosphokinase
pyrA: carbamoylphosphate synthase
pyrB: aspartate carbamoyl transferase
pyrC: dihydroorotase
pyrD: dihydroorotate oxydase
pyrE: orotate phosphoribosyl transferase
pyrF: orotidine 5'-phosphate decarboxylase
pyrG: CTP synthetase
pyrH: UMP kinase FIG. 1*b*) the conservation or recycling route which is much less costly in terms of energy and involving transfer reactions of sugar from preformed bases (originating from the hydrolytic degradation of amino acids and nucleotides). The abbreviations used are as follows (enzymes represented by their corresponding genes):
cdd: cytidine/deoxycitidine deaminase
cmk: CMP/dCMP kinase horylase
codA: cytosine deaminase
deoA: thymidine phosphorylase tdk: thymidine kinase
udk: uridine/cytidine kinase
udp: uridine phosphorylase
upp: uridine phosphoryl transferase
thyA: thymidylate synthase FIG. 2: Catalytic cycle of NTD FIG. 3: Alignment of Ntd sequences (SEQ ID NOS 25-32 disclosed respectively in order of appearance) showing the residues Y(Tyr)13, D(Asp)77, D(Asp)97, E(Glu)103 and M(Met)132 forming part of the catalytic site. Lh: *Lactobacillus helveticus*; La: *Lactobacillus acidophilus*, Lj: *lactobacillus johnsonni*, Ll: *Lactobacillus leichmann* Lf: *Lactobacillus fermentum*, Lm: *leuconostoc mesenteroides*, Pro mar: *prochlorococcus marinus*

EXAMPLE 1

Enzymatic Synthesis of Nucleosides

The synthesis of the nucleosides in *E. coli* can be carried out according to two processes; [Agnete MUNCH-PETERSEN (1983). "Metabolism of nucleotides, nucleosides and nucleobases in microorganisms" published by Academic Press] (see FIGS. 1a and 1b).

Two classes of enzymes exist which catalyze the transfer of a 2-deoxyribosyl to a nitrogenous base; see hereafter and [Jane R. HANRAHAN & David W. HUTCHINSON (1992). "The enzymatic synthesis of antiviral agents". Journal of Biotechnology; vol. 23; 193-210. The latter are sometimes used for the synthesis of nucleoside analogues].

The N-deoxyribosyl transferases catalyze the cleavage of the glycosidic bonds of the 2-deoxynucleotides. They are present in certain micro-organisms which possess little or no purine and pyrimidine phosphorylase (lactobacilla for example) [6-8]. They participate in the recycling of nucleotides.

Reactions Catalyzed According to the Type of Enzymes

Two types of enzyme have been characterized, [José HOLGUIN & Robert CARDINAUD (1975). "Trans-N-Deoxyribosylase: substrate-specific studies". European Journal of Biochemistry; vol. 54; 515-520].

Purine deoxyribosyl transferase or NTD1:

It catalyzes exclusively the reversible transfer of a sugar from a puric base (donor base) to another purine base (acceptor base).

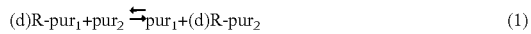

(1)

Pyrimidine/Purine deoxyribosyl transferase or NTD II

It mostly catalyzes the transfer between purine and pyrimidine according to the following reversible equations:

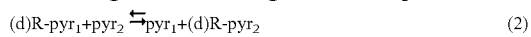

(2)

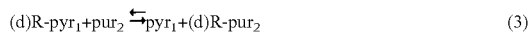

(3)

Reaction Mechanism (FIG. 2)

If we keep to what is known from *Lactobacillus delbruckii*, NTD II would react according to a "ping-pong-bi-bi" mechanism which would involve two substrates and two products [Jose HOLGUIN & Robert CARDINAUD (1975). "Trans-N-Deoxyribosylase: Purification by affinity chromatography and characterisation". European Journal of Biochemistry; vol. 54; 505-514; C. DANZIN & Robert CARDINAUD (1974). "Deoxyribosyl transfer catalysis with trans-N-deoxyribosylase. Kinetic studies of purine to purine trans-N-deoxyribosylase. European Journal of Biochemistry; vol. 48; 255-252; C. DANZIN & Robert CARDINAUD (1976). "Deoxyribosyl transfer catalysis with trans-N-deoxyribosylase. Kinetic studies of purine (pyrimidine) to purine (pyrimidine) trans-N-deoxyribosylase. European Journal of Biochemistry; vol. 62; 356-372].

It is assumed that the sugar of the donor nucleoside (dBase$_1$) binds to the enzyme covalently. An intramolecular reaction within this binary complex allows the cleavage of the β-glycosidic bond and the formation of a ternary complex E-deoxyribosyl-Base$_1$ followed by the release of the first product (Base$_1$). The acceptor base (Base$_2$) then binds to the binary intermediate and after intramolecular reaction on the active site of the enzyme, the second product (dBase$_2$) is released. The enzyme can then carry out another catalysis.

Physico-Chemical Properties

In *Lactobacillus delbruckii*, the two enzymes have a similar molecular weight (evaluated at about 100 kDa) but they differ in their thermal stability (activity observed up to 45° C. for NTD I et 55° C. for NTD II) and their optimum pH (6.4 for NTD I and 6.0 for NTD II).

The ntd gene of *Lactobacillus delbruckii* coding for NTD II with a length of 471 bp codes for the synthesis of a protein with 157 amino acids and total molecular weight of 110 kDa [William J. COOK, Steven A. SHORT & Steven E. EALICK (1990). "Crystallization & preliminary X-ray investigation of recombinant *Lactobacillus leichmanii* nucleoside 2-deoxyribosyl transferase". The Journal of Biological Chemistry; vol. 265; No. 5; 2682-2683]. The crystalline structure of the enzyme NTD II of *L. delbruckii* was determined with a resolution of 2.5 Å. This is a hexamer (trimer of dimers) constituted by six identical sub-units of 18 kDa. Each sub-unit possesses in the centre a parallel β-sheet comprising five strands of various lengths and surrounded by four a helices arranged asymmetrically. Each comprises an active site, but the six catalytic centres, approximately 20 Å distant in pairs, require the participation of the side chains of the adjacent sub-units [Shelly R. ARMSTRONG, William J. COOK, Steven A. SHORT & Steven E. EALICK (1996). "Crystal structures of nucleoside 2-deoxyribosyl transferase in native & ligand-bound forms reveal architecture of the active site". Structure; vol. 4; No. 1; 97-107]. The latter are involved in the positioning of the catalytic amino acid (glutamate 98) [David J. T. PORTER, Barbara M. MERRIL & Steven A. SHORT (1995). "Identification of the active site nucleophile nucleoside 2-deoxyribosyl transferase as glutamic acid 98". The Journal of Biological chemistry; vol. 270; No. 26; 15551-15556].

Enzymatic Synthesis of Nucleoside Analogues

The highly stereospecific transfer reactions, in the presence of an NTD I or NTD II transferase, exclusively produce the β anomer of the nucleoside (which avoids the stage of separation of the α and β isomers).

The enzyme possesses a great specificity vis-à-vis 2'-deoxyribonucleotides but tolerates a large number of modified analogues on the sugar or on the base. Thymidine and cytosine seem to be the most effective donors of sugar. On the other hand the transfer can be made to a large panel of acceptor bases. There can for example be mentioned the purines substituted in position 6 [D. BETBEDER, D. W. HUTCHINSON & A. O. RICHARDS (1989). "The stereoselective enzymatic synthesis of 9-β-D-2',3'-dideoxynucleosides of N(6) substituted purines". Antiviral Chem. Chemother; vol. 17; 4217-4222] and dYTP.

dYTP:

The imidazole-4-carboxamide called Y was proposed as simplified purine. This analogue has the formula:

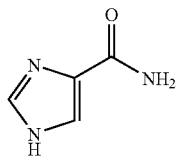

It has been reported that the nucleotide dYTP could be substituted for dATP or dGTP during the copying of the DNA which introduces mutations. There can also be mentioned the compounds described in WO 01/96354 (Institut Pasteur) of general formula:

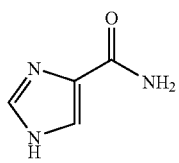

The NTD enzymes prove to be capable of marginally catalyzing the exchange reaction between a 2',3'-dideoxyribose and an acceptor base: dd-1'-Base$_1$+Base$_2$ ⇌ Base$_1$+dd-1'-Base$_2$ (dd=2',3'-dideoxyribose)

Nevertheless the speed of this transfer remains very low compared to that characterizing the exchange of deoxyriboses.

The 2',3'-dideoxyribonucleotides are evidently useful as chain terminators in the sequencing procedures. Furthermore, 2',3'-dideoxyadenosine (ddA) and 2',3'-dideoxyinosine (ddI) are used for therapeutic purposes in particular in the case of the AIDS virus: these analogues effectively inhibit the replication of HIV (human immunodeficiency virus) [H. MITSUYA & S. BRODER (1987)."Strategies for antiviral therapy in AIDS". Nature; vol. 325; 773-778].

To this end, the invention provides a novel method for obtaining mutants of the NTD II enzyme in order to select mutant enzymes of L. fermentum which have a stronger specificity towards the 2',3'-dideoxyribonucleosides than the native enzyme.

EXAMPLE 2

Application of the Method According to the Invention for Obtaining Ntd*

Materials and Methods

The PAK9 E. coli strains are cultured in Luria-Bertani (LB) medium or in minimum MS medium (Richaud et al. 1993). The antibiotics kanamycin, Km and chloramphenicol Cm, are used at a final concentration of 25 μg/ml; tetracycline, Tc and gentamycin, Gm, 10 μg/ml. The nucleosides and bases are used in the culture media at a final concentration of 0.3 mM. The molecular biology techniques are carried out according to Sambrook et al. (1989)

The amplification products are purified using QIAquick PCR purification (QIAgen)

The DNA fragments purified on agarose gel are extracted using the Jetsorb Kit (Genomed) or the QIAquick gel extraction kit (QIAgen). The plasmidic DNA is purified using the QIAprep spin miniprep kit (QIAgen)

The strain PAK9 (MG1655 ΔpyrC::Gm, ΔcodA::Km, cdd::Tn10) is available from the CNCM (Collection Nationale de Culture des Microorganismes) at the Institut Pasteur, 25-28 rue du Dr Roux 75224 Paris cedex 15, under No. 1-2902.

The vector pSU19N was obtained by site-directed mutagenesis of the plasmid pSU19 [B. BARTOLOME, J. JUBETE, E. MARTINEZ & F. DE LA CRUZ (1991) "Constructions and properties of a family of pACYC184-derived cloning vectors compatible with pBR322 and its derivatives" Gene; vol. 102; 75-78; E. MARTINEZ, B. BARTOLOME & F. DE LA CRUZ (1988) "pACYC184-derived cloning vectors containing the multiple cloning site and lacZ alpha reporter gene of pUC8/9 and pUC18/19 plasmids" Gene; vol 68(1); 159-162] using the oligonucleotides (SEQ. ID No. 5)
PAK 23 5'P-CAATTTCACACAGGAAACACATATGACCATGATTACGCC (SEQ. ID No. 6)
PAK 24 5'P-TGTTTCCTGTGTGAAATTGTTATCCGCTCAC An ntd gene of L. fermentum was amplified by PCR from the plasmid pLF6 used here as DNA matrix. The plasmid pLF6 propagated from the E. coli strain PAK6 deposited at the CNCM on 2 May 2001 under the reference 1-2664, contains a fragment Alu I of 1.36 kb of the gene encoding the N-deoxyribosyl transferase of type II originating from the strain L. fermentum CIP102780T. In order to amplify this DNA fragment, the following oligonucleotides were used:

(SEQ. ID No. 7)
PAK 5 5'-GATATACATATGAAAAATACCGACCCAGTTGC
and (SEQ. ID No. 8)
PAK 6 5'-NNGGATCCTTAGGTTAGTTAGAAAACCTTGAATGGTGGG, then the amplified fragments were digested by the restriction enzymes BamHI and NdeI and cloned in the vector pSU19N. In this construction, the expression of the protein is under the control of the lac promoter.

1) Mutagenesis

The primers T7prom (5'-TTAATACGACTCACTATAGGGG)(SEQ ID No.9) and T7term (5'-GCTAGTTATTGCTCAGCGG) (SEQ ID No.10) were used to amplify the ntd gene cloned in the plasmid pET24a (Novagen) according to standard amplification conditions using the GeneMorph PCR Mutagenesis Kit (Stratagene, USA). The amplification parameters: 1 cycle of 5' at 95° C., 30 cycles each comprising the following three stages: 30" at 95° C., 30" at 51.5° C., 1' at 72° C., then a cycle of 10' at 72° C. The concentrations of DNA matrix used: 10 ng and 10 pg.

2) Cloning and Selection

The purified amplification products are digested for 2 hours at 37° C. by the restriction enzymes BamHI and NdeI. After migration at 150V for 45 minutes, they are purified by 1% agarose gel extraction using the QIAquick gel extraction kit (QIAgen).

The plasmid pSU19N is digested by the same enzymes and purified according to the same procedure.

The ligations produced in a volume of 20 μl comprise 15 ng of the amplification products, 50 ng of pSU19 digested by BamHI-HindIII, 2 μl of 10× concentrated reaction buffer of T4 DNA ligase and 6U of T4 DNA ligase. The reaction is carried out at 16° C. for 18 hours.

The ligation products are then dialysed on Millipore filter (0.05 μm; 13 mm) for 30 minutes then used to transform the strain PAK9, prepared according to the protocol described by Dower et al. (1987), by electroporation.

1 to 5 μl of ligated DNA mixed with 50 μl of the strain PAK9 in a 2 mm cuvette are subjected to a charge of 2.5 kV. After incubation for one hour at 37° C. in 1 ml of LB medium supplemented with uracil (0.3 mM), two successive washings with 1 ml of 1× MS medium are carried out.

450 μl of suspension are plated on mineral glucose agar medium supplemented with Cm, ddU and C. The dishes are incubated at 37° C. for 4 days. The selected colonies are then isolated on the same medium.

The plasmid DNA of the isolated colonies is prepared from cultures in LB medium supplemented with Cm and U. The sequencing of the plasmids was carried out by the company MWG-BIOTECH.

The sequencing of the plasmids present in the selected transformants of PAK 9 made it possible to identify a mutation in the sequence (ntd) having the effect of substituting a residue T for the residue A in position 15 in the corresponding protein sequence (SEQ ID No. 2) (mutation called A15T).

3) Measurement of the Enzymatic Activity of the Crude Extracts of the Different Mutants 3.1 Preparation of the Crude Extracts The precultures are obtained after inoculation of an isolated colony in 5 ml of LB medium containing Cm and U for the strain PAK9 followed by incubation overnight under stirring at 37° C.

The next day, 15 ml of LB medium containing Cm and U are inoculated at an $OD_{600}$=0.01. The cultures are then incubated at 37° C. up to an OD comprised between 0.8 and 1.

The cells are then centrifuged at 4000 rpm for 30 minutes at 4° C., the pellet is resuspended in 10 ml of phosphate buffer ($Na_2HPO_4+NaH_2PO_4$) at 50 mM (pH=7.5). After centrifugation, the pellet is resuspended in 1 ml of the same buffer. The cells, preserved in ice, are then subjected to three cycles of 30 s of sonication and 30 s of rest. After centrifugation at 12000 rpm for 2×15 minutes at 4° C., the supernatants are recovered and stored at −20° C.

3.2 Enzymatic Reaction

50 μl of enzymatic extract is added to 200 μl of 100 mM citrate buffer, pH 6.44, in the presence of 3 mM ddU or dU final and of 1 mM C final for the strain PAK9, the whole is incubated at 37° C. The progress of the reaction is monitored by TLC (silica; eluent: MeOH—$CH_2Cl_2$ (20/80)). The products are revealed under UV, and the sugars revealed by Zücker reagent. The disappearance of the substrates and the formation of the products were also quantified by HPLC analysis. The different products are separated by analytical HPLC with a reversed-phase column (100-5C18) using a flow rate of 1 ml/min and a linear gradient of 5-25% $CH_3CN$ in a 10 mM triethyl ammonium acetate buffer at pH 7.5 for 20 minutes.

4) Overproduction and Purification of the Native N-Deoxyribosyl Transferase and the Mutant LFA15T.

The oligonucleotides:

(SEQ ID No. 11)
PAK 5   5'-NGATATA<u>CATATG</u>AAAAATACCGACCCAGTTGC
and (SEQ ID No. 12)
PAK 6   5'NN<u>GGATCC</u>TTAGGTTAGTTAGAAAACCTTGAATGGTGGG were used as primer in an amplification reaction under standard conditions using the ntd gene of *L. fermentum* cloned in pSU19 (pLF6) as DNA matrix. The amplification product was digested by the restriction enzymes Nde1 and BamH1 for 2 hours at 37° C., purified on agarose gel and inserted into the plasmid pET24a digested by the same enzymes then the ligation mixture is used to transform the strain β 2033. The plasmid DNA from the colonies was prepared and digested by the enzymes Nde1 and BamH1. Those, the sequence of which was correct, were used to transform the strain BL21 (DE3)/plysS (Novagen). The plasmid DNA of the mutant pSU19NLFA15T selected previously was prepared then digested by the enzymes Nde1 and BamH1. The corresponding fragment Nde1-BamH1 was then inserted into the plasmid pET24a digested by the same enzymes in order to produce the expression plasmid pETLFA15T useful to the expression of the mutated protein. A strain of *E. coli* transformed using the plasmid pETLFA15T was deposited at the CNCM (INSTITUT PASTEUR, 25 rue du Docteur Roux, F-75724 PARIS Cedex 15) on 22 Mar. 2004 under accession number I-3192. The overproduction of the two N-deoxyribosyl transferases, native and mutated, was obtained from cultures of this strain in 500 ml of LB medium supplemented with Km and Cm. These cultures were induced at an $OD_{600}$=0.6 by the addition of IPTG (0.4 mM), the incubation being continued for 2 hours 30 minutes at 37° C.

The cells are then centrifuged for 15' at 4000 rpm at 4° C., washed in 50 ml of phosphate buffer then the pellet obtained after centrifugation is preserved overnight at −20° C. The bacterial pellet resuspended in 20 ml of phosphate buffer is then lysed by passage through a French press at 14000 psi. The lysate is centrifuged for 90' at 50,000 rpm. The supernatant containing the soluble proteins is then precipitated with ammonium sulphate (40% saturation). The precipitate obtained after centrifugation at 13900 rpm (20,000 g) for 30' at 4° C. is resuspended in 1 ml of 100 mM phosphate buffer, pH 7.5, 1.5 M NaCl, then deposited on a Sephacryl S200 gel filtration column (Amersham-Pharmacia). The fractions are then analyzed by SDS-PAGE gel and the enzymatic activity determined. The most active and purest fractions are dialysed overnight at 4° C. against the same buffer at pH=6.0. The protein concentration is determined by measuring the OD at 280 nm.

The measurement of the enzymatic activities is carried out as described in paragraph 4.2.

5) Results

The transforming clones of the *E. coli* strain PAK9, expressing the mutated ntd gene of *L. fermentans* were selected in glucose mineral medium with dideoxyuracil (ddR-U) and cytosine (C) added.

Several transformants were obtained and are capable of carrying out the exchange:

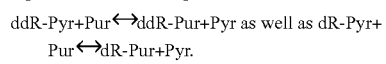

The nucleotide sequences of the different variants of ntd are identical and only differ from the wild-type gene by one mutation (indicated in bold type in Table 2 below). In both cases (*L. leichmannii* and *L. fermentum*) a neutral amino acid (glycine and alanine) is replaced by a nucleophilic amino acid (serine and threonine respectively). The conversion of N-deoxyribosyl transferase to N-dideoxyribosyl transferase or N-didehydroribosyl transferase therefore seems to require the substitution of a neutral amino acid by a nucleophilic amino acid which must contribute to the positioning of the sugar promoting its catalysis. It is interesting to note in Table 2 that all the N-deoxyribosyl transferases as well as a certain number of homologous proteins (of unknown function) possess a glycine or an alanine in this position.

enzyme mutated according to the method of the invention shows a better catalytic activity on d4T and on ddT than the native enzyme. The activities are increased respectively by

TABLE 2

(SEQ ID NOS 13-24 are disclosed respectively in order of appearance)

| Origin of the mutated gene | Corresponding protein sequence | |
|---|---|---|
| NTD Lactobacillus. acidophilus | MMAKTKTLYF G | AGWFNEKQNKAYKAAMEALKQN |
| NTD Lactobacillus. helveticus | MNKKKTLYF G | AGWFNEKQNKAYKEAMAALKEN |
| NTD Lactobacillus. leichmannii | MPKKTIYF G | AGWFTDRQNKAYKEAMEALKEN |
| NTD LIG9S | MPKKTIYF S | AGWFTDRQNKAYKEAMEALKEN |
| PTD Lactobacillus. helveticus | MKAVVPTG-KIYL G | SPFYSDAQRERAAKAKELLAKN |
| Lactobacillus gasseri | MTKQKTVYF G | AGWFTETQNKAY |
| NTD Lactobacillus. fermentum | LKNTDPVANTKIYL A | TSFFNEEQRARIPQALAQLEAN |
| NTDLFA15T | LKNTDPVANTKIYL T | TSFFNEEQRARIPQALAQLEAN |
| Oenococcus oeni MCW | MNMAKNIYL A | SPFFDDEQIARVKKIEKALESN |
| Leuconostoc mesenteroides ATCC 8293 | KNVYL A | SPFFDKEQIERVERVEKALAAN |
| Lactobacillus plantarum WCFS1 | VYL A | APFFDEAQKERIQQVKSALLAN |
| Lactococcus lactis IL 1403 | NQAVNVYL A | APFFSESQIKK |

The enzymatic activities of the native and mutant N-deoxyribosyl transferases of L. leichmannii (LL and LL G9S) and of L. fermentum (LF and LFA15T) in the exchange reactions dT+C↔dC+T, ddT+C↔ddC+T and d4T+C↔d4C+T were evaluated starting from crude extracts or purified proteins.

The results reported in Table 3 below show that the specific activity of the mutant LFA15T is less than that of the native enzyme (LF) for the transfer of deoxyribose but that the latter is greater for the transfer of dideoxyribose or didehydroribose. For the transfer of deoxyribose, the activity is reduced by a factor of 7, whereas the latter is increased by 3 in the case of the transfer of dideoxyribose and by 35 in the case of didehydroribose.

TABLE 3

| | LL | LL G9S | LF | LFA15T |
|---|---|---|---|---|
| dT + C | 100 | 10 | 76.5 | 10.7 |
| ddT + C | 0.2 | 2.5 | 0.9 | 2.5 |
| d4T + C | 0.5 | 8 | 2.1 | 73.5 |

Note:
100% at the top of the LL column represents the specific activity of the enzyme NTD of L. leichmannii during the reaction dT + C ↔ dC + T.

Table 4 below shows in detail the results of enzymatic activity tests for the native enzyme and the mutated enzyme of B. fermentum for each of the dT+C, ddT+C and d4T+C reactions. The first column of the table shows the affinity constant values (Km), the second the maximum reaction speed (Vmax), the third, the catalysis constant (Kcat), and the last the ratio of the affinity and catalysis constants (Km/Kcat) taking account of the effectiveness of the enzymes tested. These different values were measured according to the protocol described in the literature [P A Kaminski (2002) "Functional cloning, heterologous expression and purification of two different N-deoxyribosyl transferases from Lactobacillus helveticus" J. Biol. Chem; vol. 277; 14400-14407]. The 60% and 54%. Moreover, the mutated enzyme LFA15T is 60 times more effective than the native enzyme LF in the ddT+X exchange and 7.5 times more effective in the d4T+X exchange.

TABLE 4

| | Km µM | Vmax µmol/s | Kcat µmol/s/µg | Kcat/km |
|---|---|---|---|---|
| LF dT | 124 | 6.65 | 0.665 | 5.36 |
| LF ddT | 80 | 5.7 | 0.038 | 0.047 |
| LF d4T | 1250 | 24 | 0.56 | 0.448 |
| LFA15T dT | 371 | 9.7 | 0.242 | 0.65 |
| LFA15T ddT | 53 | 7.8 | 0.156 | 2.9 |
| LFA15Td4T | 1.1 | 18.4 | 3.68 | 3.34 |

The selected enzyme is therefore used in the enzymatic synthesis of 2',3'-dideoxynucleosides and 2',3'-dideoxy, 2',3'-didehydronucleosides from natural bases ddC, ddA, ddI, d4T, d4C, d4G (Ray et al. 2002; Stuyver et al. 2002) or modified bases (Pokrovsky et al. 2001 Chong et al., 2002) such as (1β-3'-fluoro) 2',3'-dideoxy, 2',3'-didehydro-4'-thio-Nucleosides comprising or not comprising radioelements.

6) Determination of the Residues Involved in the Catalytic Site of the Enzyme Ntd:

As shown by the alignment of FIG. 3, the residues Y(Tyr)13, D(Asp)77, D (Asp)97, E(Glu)103 and M(Met)132 (numbering established in relation to Ntd of B. fermentum—SEQ ID No. 2) are to be found particularly well-preserved in the Ntd proteins of the different microorganisms represented. Point mutagenesis experiments targeting these residues have made it possible to establish that they were involved in the catalytic site of the enzyme. In fact, the mutation of one of these residues results in a loss of activity of the enzyme of the order of 90%.

REFERENCES

Bartolome B, Jubete Y, Martinez E, de la Cruz F. (1991) Construction and properties of a family of pACYC184-derived cloning vectors compatible with pBR322 and its derivatives. *Gene.* 102: 75-8

Carson D. A. & Wasson D. B. (1988) Synthesis of 2',3'-dideoxynucleosides by enzymatic trans-glycosylation. *Biochem. Biophys. Res. Comm.* 155: 829-834.

Chong Y, Choo H, Choi Y, Mathew J, Schinazi R F, Chu C K. Stereoselective synthesis and antiviral activity of D-2',3'-didehydro-2',3'-dideoxy-2'-fluoro-4'-thionucleosides. *J Med Chem.* 2002 45: 4888-98.

Dower W J, Miller J F, Ragsdale C W. (1988) "High efficiency transformation of *E. coli* by high voltage electroporation." *Nucleic Acids Res.* 16: 6127-45.

Fischer, X., Kaun, E. and Genz, U. (1990) 2',3'-Dideoxyribofuranosides and method for their production. Ger. Offen. DE 3840160.

Pokrovsky A G, Pronayeva T R, Fedyuk N V, Shirokova E A, Khandazhinskaya A L, Tarusova N B, Karpenko I L, Krayevsky A A. (2001) Anti-HIV activity of novel phosphonate derivatives of AZT, d4T, and ddA. *Nucleosides Nucleotides Nucleic Acids.* 4-7: 767-9.

Ray A S, Yang Z, Chu C K, Anderson K S. Novel use of a guanosine prodrug approach to convert 2',3'-didehydro-2',3'-dideoxyguanosine into a viable antiviral agent. *Antimicrob Agents Chemother.* 2002 46: 887-91.

Richaud C, Mengi N, Lecreuix D, Pochet S, Johnson E J, Cohen G N, Marliere P. (1993) Directed evolution of biosynthetic pathways. Recruitment of cysteine thioethers for constructing the cell wall of *Escherichia coli*. *J Biol Chem.* 268: 26827-35.

Secrist J A 3rd, Riggs R M, Tiwari K N, Montgomery J A. Synthesis and anti-HIV activity of 4'-thio-2',3'-dideoxynucleosides. *J Med Chem* 1992 35: 533-8

Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogues. *Antimicrob Agents Chemother.* 2002 46: 3854-60.

Van Draanen N A, Freeman G A, Short S A, Harvey R, Jansen R, Szczech G, Koszalka G W. (1996) "Synthesis and antiviral activity of 2'-deoxy-4'-thio purine nucleosides." *J Med Chem* 39: 538-42

The invention claimed is:

1. An isolated N-deoxyribosyl transferase protein (DTP) that has at least 90% identity with the polypeptide of SEQ ID NO: 2 or SEQ ID NO: 4, but which is not SEQ ID NO: 2; that retains residues Y13, D77, D97, E103, and M132 that respectively correspond to positions 13, 77, 97, 103, and 132 of SEQ ID NO: 2; and that has threonine at a position corresponding to position 15 of SEQ ID NO: 2 or SEQ ID NO: 4, and which has N-deoxyribosyl transferase activity.

2. The protein according to claim 1, which is at least 95% identical with SEQ ID NO: 2.

3. The protein according to claim 1 which is at least 95% identical to SEQ ID NO: 4.

4. The protein according to claim 1, which is at least 98% identical to SEQ ID NO: 4.

5. The protein according to claim 1, which is at least 98% identical to SEQ ID NO: 2.

6. The protein according to claim 1, which comprises SEQ ID NO: 4.

7. The protein according to claim 1, which has a N-dideoxyribosyl transferase activity.

8. The protein according to claim 1, wherein said protein has a deoxyribose and dideoxyribose and/or didehydroribose transfer activity.

9. The protein according to claim 1, wherein said protein has a catalytic activity on d4T and ddT greater than that of the native N-deoxyribosyl transferase protein of *L. fermentum* represented by comprising SEQ ID NO: 2.

10. The protein according to claim 9, wherein said catalytic activity on d4T and ddT is 50% greater than that of the native N-deoxyribosyl transferase protein of *L. fermentum* comprising SEQ ID NO: 2.

11. The protein according to claim 1, wherein said protein has a catalytic effectiveness on d4T and ddT greater than that of the native N-deoxyribosyl transferase protein of *L. fermentum* comprising SEQ ID NO: 2.

12. The protein according to claim 11, wherein said catalytic effectiveness on d4T and ddT is at least 5 times greater than that of the native N-deoxyribosyl transferase protein of *L. fermentum* comprising SEQ ID NO: 2.

13. The protein according to claim 1, wherein the protein consists of a polypeptide of sequence SEQ ID NO: 4.

14. An isolated or purified nucleic acid that encodes the protein according to claim 1.

15. An expression vector comprising the nucleic acid according to claim 14.

16. The vector according to claim 15, further comprising a promoter effective in a eukaryotic or prokaryotic cell for expressing said nucleic acid.

17. The vector according to claim 15, which is a plasmid capable of transforming and being maintained in *E. coli*.

18. A host cell comprising a vector according to claim 15.

19. A method for transferring a dideoxyribose (ddR) from a dideoxynucleoside to another nucleoside, comprising:
    contacting the dideoxynucleoside with a protein having an N-dideoxyribosyl transferase activity according to claim 1.

20. The method according to claim 19, further comprising synthesizing a 2',3'-dideoxynucleoside.

21. The method according to claim 19, further comprising synthesizing a 2',3'-didehydro-2',3'-dideoxynucleoside.

22. A strain of *E. coli* deposited at the CNCM on 22 Mar. 2004 under accession number 1-3192.

* * * * *

SEQUENCE LISTING

<160> NUMBER OF SEQ ID NOS: 32

<210> SEQ ID NO 1
<211> LENGTH: 504
<212> TYPE: DNA
<213> ORGANISM: Lactobacillus fermentum

<400> SEQUENCE: 1

```
atgaaaaata ccgacccagt tgctaacact aaaatttacc tggctaccag cttcttcaac      60
gaagaacaac gtgcccgcat ccctcaagct ctagcccaac tagaagccaa cccgactgtc     120
ggcgttgttc accagccatt cgatttccaa tataaagatg cacgcgtaga ctccgatcct     180
gccggcgtct ttggcagcct cgaatggcaa attgccactt acaataacga cctcaacgcg     240
gtaggaactt ccgatgtctg cgttgcttta tacgatatgg accaaattga cgaaggaatt     300
tgtatggaaa tcggcatgtt cgtcgccctc cataaaccta tcgttttact accttttact     360
aagaaagata agtctgctta tgaagctaac ctaatgctag cacggggtgt aactacctgg     420
ttggaaccta atgactttag tcccttaaaa gactttaact ttaaccaccc aatggctcaa     480
cctttcccac cattcaaggt tttc                                            504
```

<210> SEQ ID NO 2
<211> LENGTH: 168
<212> TYPE: PRT
<213> ORGANISM: Lactobacillus fermentum

<400> SEQUENCE: 2

```
Met Lys Asn Thr Asp Pro Val Ala Asn Thr Lys Ile Tyr Leu Ala Thr
 1               5                  10                  15

Ser Phe Phe Asn Glu Glu Gln Arg Ala Arg Ile Pro Gln Ala Leu Ala
            20                  25                  30

Gln Leu Glu Ala Asn Pro Thr Val Gly Val Val His Gln Pro Phe Asp
        35                  40                  45
```

```
Phe Gln Tyr Lys Asp Ala Arg Val Asp Ser Asp Pro Ala Gly Val Phe
    50                  55                  60
Gly Ser Leu Glu Trp Gln Ile Ala Thr Tyr Asn Asn Asp Leu Asn Ala
 65              70                  75                  80
Val Gly Thr Ser Asp Val Cys Val Ala Leu Tyr Asp Met Asp Gln Ile
                 85                  90                  95
Asp Glu Gly Ile Cys Met Glu Ile Gly Met Phe Val Ala Leu His Lys
            100                 105                 110
Pro Ile Val Leu Leu Pro Phe Thr Lys Lys Asp Lys Ser Ala Tyr Glu
        115                 120                 125
Ala Asn Leu Met Leu Ala Arg Gly Val Thr Thr Trp Leu Glu Pro Asn
    130                 135                 140
Asp Phe Ser Pro Leu Lys Asp Phe Asn Phe Asn His Pro Met Ala Gln
145                 150                 155                 160
Pro Phe Pro Pro Phe Lys Val Phe
                165

<210> SEQ ID NO 3
<211> LENGTH: 504
<212> TYPE: DNA
<213> ORGANISM: Lactobacillus fermentum

<400> SEQUENCE: 3
atgaaaaata ccgacccagt tgctaacact aaaatttacc tgactaccag cttcttcaac      60
gaagaacaac gtgcccgcat ccctcaagct ctagcccaac tagaagccaa cccgactgtc     120
ggcgttgttc accagccatt cgatttccaa tataaagatg cacgcgtaga ctccgatcct     180
gccggcgtct ttggcagcct cgaatggcaa attgccactt acaataacga cctcaacgcg     240
gtaggaactt ccgatgtctg cgttgcttta tacgatatgg accaaattga cgaaggaatt     300
tgtatggaaa tcggcatgtt cgtcgccctc cataaaccta tcgttttact accttttact     360
aagaaagata agtctgctta tgaagctaac ctaatgctag cacggggtgt aactacctgg     420
ttggaaccta atgactttag tcccttaaaa gactttaact ttaaccaccc aatggctcaa     480
cctttcccac cattcaaggt tttc                                            504

<210> SEQ ID NO 4
<211> LENGTH: 168
<212> TYPE: PRT
<213> ORGANISM: Lactobacillus fermentum

<400> SEQUENCE: 4

Met Lys Asn Thr Asp Pro Val Ala Asn Thr Lys Ile Tyr Leu Thr Thr
  1               5                  10                  15
Ser Phe Phe Asn Glu Glu Gln Arg Ala Arg Ile Pro Gln Ala Leu Ala
                 20                  25                  30
Gln Leu Glu Ala Asn Pro Thr Val Gly Val Val His Gln Pro Phe Asp
             35                  40                  45
Phe Gln Tyr Lys Asp Ala Arg Val Asp Ser Asp Pro Ala Gly Val Phe
    50                  55                  60
Gly Ser Leu Glu Trp Gln Ile Ala Thr Tyr Asn Asn Asp Leu Asn Ala
 65              70                  75                  80
Val Gly Thr Ser Asp Val Cys Val Ala Leu Tyr Asp Met Asp Gln Ile
                 85                  90                  95
Asp Glu Gly Ile Cys Met Glu Ile Gly Met Phe Val Ala Leu His Lys
            100                 105                 110
```

```
Pro Ile Val Leu Leu Pro Phe Thr Lys Lys Asp Lys Ser Ala Tyr Glu
        115                 120                 125
Ala Asn Leu Met Leu Ala Arg Gly Val Thr Thr Trp Leu Glu Pro Asn
130                 135                 140
Asp Phe Ser Pro Leu Lys Asp Phe Asn Asn His Pro Met Ala Gln
145                 150                 155                 160
Pro Phe Pro Pro Phe Lys Val Phe
                165

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caatttcaca caggaaacac atatgaccat gattacgcc                            39

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgtttcctgt gtgaaattgt tatccgctca c                                   31

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatatacata tgaaaaatac cgacccagtt gc                                  32

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, t, c, g, unknown or other

<400> SEQUENCE: 8
nnggatcctt aggttagtta gaaaaccttg aatggtggg                            39

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
```

```
ttaatacgac tcactatagg gg                                            22
```

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
gctagttatt gctcagcgg                                                19
```

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: a, t, c, g, unknown or other

<400> SEQUENCE: 11

```
ngatatacat atgaaaaata ccgacccagt tgc                                33
```

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, t, c, g, unknown or other

<400> SEQUENCE: 12

```
nnggatcctt aggttagtta gaaaaccttg aatggtggg                          39
```

<210> SEQ ID NO 13
<211> LENGTH: 33
<212> TYPE: PRT
<213> ORGANISM: Lactobacillus acidophilus

<400> SEQUENCE: 13

Met Met Ala Lys Thr Lys Thr Leu Tyr Phe Gly Ala Gly Trp Phe Asn
 1               5                  10                  15

Glu Lys Gln Asn Lys Ala Tyr Lys Ala Ala Met Glu Ala Leu Lys Gln
             20                  25                  30

Asn

<210> SEQ ID NO 14
<211> LENGTH: 32
<212> TYPE: PRT
<213> ORGANISM: Lactobacillus helveticus

<400> SEQUENCE: 14

Met Asn Lys Lys Lys Thr Leu Tyr Phe Gly Ala Gly Trp Phe Asn Glu
 1               5                  10                  15

Lys Gln Asn Lys Ala Tyr Lys Glu Ala Met Ala Ala Leu Lys Glu Asn
             20                  25                  30

```
<210> SEQ ID NO 15
<211> LENGTH: 31
<212> TYPE: PRT
<213> ORGANISM: Lactobacillus leichmannii

<400> SEQUENCE: 15

Met Pro Lys Lys Thr Ile Tyr Phe Gly Ala Gly Trp Phe Thr Asp Arg
  1               5                  10                  15

Gln Asn Lys Ala Tyr Lys Glu Ala Met Glu Ala Leu Lys Glu Asn
             20                  25                  30

<210> SEQ ID NO 16
<211> LENGTH: 31
<212> TYPE: PRT
<213> ORGANISM: Lactobacillus leichmannii

<400> SEQUENCE: 16

Met Pro Lys Lys Thr Ile Tyr Phe Ser Ala Gly Trp Phe Thr Asp Arg
  1               5                  10                  15

Gln Asn Lys Ala Tyr Lys Glu Ala Met Glu Ala Leu Lys Glu Asn
             20                  25                  30

<210> SEQ ID NO 17
<211> LENGTH: 35
<212> TYPE: PRT
<213> ORGANISM: Lactobacillus helveticus

<400> SEQUENCE: 17

Met Lys Ala Val Val Pro Thr Gly Lys Ile Tyr Leu Gly Ser Pro Phe
  1               5                  10                  15

Tyr Ser Asp Ala Gln Arg Glu Arg Ala Ala Lys Ala Lys Glu Leu Leu
             20                  25                  30

Ala Lys Asn
         35

<210> SEQ ID NO 18
<211> LENGTH: 22
<212> TYPE: PRT
<213> ORGANISM: Lactobacillus gasseri

<400> SEQUENCE: 18

Met Thr Lys Gln Lys Thr Val Tyr Phe Gly Ala Gly Trp Phe Thr Glu
  1               5                  10                  15

Thr Gln Asn Lys Ala Tyr
             20

<210> SEQ ID NO 19
<211> LENGTH: 37
<212> TYPE: PRT
<213> ORGANISM: Lactobacillus fermentum

<400> SEQUENCE: 19

Leu Lys Asn Thr Asp Pro Val Ala Asn Thr Lys Ile Tyr Leu Ala Thr
  1               5                  10                  15

Ser Phe Phe Asn Glu Glu Gln Arg Ala Arg Ile Pro Gln Ala Leu Ala
             20                  25                  30

Gln Leu Glu Ala Asn
         35

<210> SEQ ID NO 20
<211> LENGTH: 37
```

```
<212> TYPE: PRT
<213> ORGANISM: Lactobacillus fermentum

<400> SEQUENCE: 20

Leu Lys Asn Thr Asp Pro Val Ala Asn Thr Lys Ile Tyr Leu Thr Thr
  1               5                  10                  15

Ser Phe Phe Asn Glu Glu Gln Arg Ala Arg Ile Pro Gln Ala Leu Ala
             20                  25                  30

Gln Leu Glu Ala Asn
         35

<210> SEQ ID NO 21
<211> LENGTH: 32
<212> TYPE: PRT
<213> ORGANISM: Oenococcus oeni

<400> SEQUENCE: 21

Met Asn Met Ala Lys Asn Ile Tyr Leu Ala Ser Pro Phe Phe Asp Asp
  1               5                  10                  15

Glu Gln Ile Ala Arg Val Lys Lys Ile Glu Lys Ala Leu Glu Ser Asn
             20                  25                  30

<210> SEQ ID NO 22
<211> LENGTH: 28
<212> TYPE: PRT
<213> ORGANISM: Leuconostoc mesenteroides

<400> SEQUENCE: 22

Lys Asn Val Tyr Leu Ala Ser Pro Phe Phe Asp Lys Glu Gln Ile Glu
  1               5                  10                  15

Arg Val Glu Arg Val Glu Lys Ala Leu Ala Ala Asn
             20                  25

<210> SEQ ID NO 23
<211> LENGTH: 26
<212> TYPE: PRT
<213> ORGANISM: Lactobacillus plantarum

<400> SEQUENCE: 23

Val Tyr Leu Ala Ala Pro Phe Phe Asp Glu Ala Gln Lys Glu Arg Ile
  1               5                  10                  15

Gln Gln Val Lys Ser Ala Leu Leu Ala Asn
             20                  25

<210> SEQ ID NO 24
<211> LENGTH: 20
<212> TYPE: PRT
<213> ORGANISM: Lactobacillus lactis

<400> SEQUENCE: 24

Asn Gln Ala Val Asn Val Tyr Leu Ala Ala Pro Phe Phe Ser Glu Ser
  1               5                  10                  15

Gln Ile Lys Lys
         20

<210> SEQ ID NO 25
<211> LENGTH: 158
<212> TYPE: PRT
<213> ORGANISM: Lactobacillus helveticus

<400> SEQUENCE: 25

Met Asn Lys Lys Lys Thr Leu Tyr Phe Gly Ala Gly Trp Phe Asn Glu
```

```
              1               5                  10                 15
Lys Gln Asn Lys Ala Tyr Lys Glu Ala Met Ala Ala Leu Lys Glu Asn
                     20                  25                  30

Pro Thr Val Asp Leu Glu Asn Ser Tyr Val Pro Leu Glu Asn Gln Tyr
             35                  40                  45

Lys Gly Ile Arg Ile Asp Glu His Pro Glu Tyr Leu His Asn Ile Glu
     50                  55                  60

Trp Ala Ser Ala Thr Tyr His Asn Asp Leu Val Gly Ile Lys Thr Ser
65                   70                  75                  80

Asp Val Met Leu Gly Val Tyr Leu Pro Glu Glu Asp Val Gly Leu
                     85                  90                  95

Gly Met Glu Leu Gly Tyr Ala Leu Ser Gln Gly Lys Tyr Ile Leu Leu
                 100                 105                 110

Val Ile Pro Asp Glu Asp Tyr Gly Lys Pro Ile Asn Leu Met Ser Trp
             115                 120                 125

Gly Val Cys Asp Asn Ala Ile Lys Ile Ser Glu Leu Lys Asp Phe Asp
         130                 135                 140

Phe Asn Lys Pro Arg Tyr Asn Phe Tyr Asp Gly Ala Val Tyr
145                 150                 155
```

<210> SEQ ID NO 26
<211> LENGTH: 159
<212> TYPE: PRT
<213> ORGANISM: Lactobacillus acidophilus

<400> SEQUENCE: 26

```
Met Met Ala Lys Thr Lys Thr Leu Tyr Phe Gly Ala Gly Trp Phe Asn
1               5                  10                  15

Glu Lys Gln Asn Lys Ala Tyr Lys Ala Ala Met Glu Ala Leu Lys Gln
                20                  25                  30

Asn Pro Thr Val Asp Leu Glu Asn Ser Tyr Val Pro Leu Glu Asn Gln
            35                  40                  45

Tyr Lys Asp Ile Arg Val Asp Glu His Pro Glu Tyr Leu His Asp Ile
        50                  55                  60

Glu Trp Ala Ser Ala Thr Tyr His Asn Asp Leu Ile Gly Ile Lys Ser
65                  70                  75                  80

Ser Asp Ile Met Leu Gly Val Tyr Leu Pro Glu Glu Asp Val Gly
                85                  90                  95

Leu Gly Met Glu Leu Gly Tyr Ala Leu Ser Gln Gly Lys Tyr Ile Leu
            100                 105                 110

Leu Val Ile Pro Asp Glu Asp Tyr Gly Lys Pro Ile Asn Leu Met Ser
        115                 120                 125

Trp Gly Val Cys Asp Asn Ala Ile Lys Ile Ser Glu Leu Lys Asp Phe
    130                 135                 140

Asp Phe Asn Lys Pro Arg Phe Asn Phe Tyr Asp Gly Ala Val Tyr
145                 150                 155
```

<210> SEQ ID NO 27
<211> LENGTH: 149
<212> TYPE: PRT
<213> ORGANISM: Lactobacillus johnsonii

<400> SEQUENCE: 27

```
Met Ala Gly Trp Phe Thr Glu Thr Gln Asn Lys Ala Tyr Lys Asp Ala
1               5                  10                  15

Met Ser Ala Leu Asn Ala Asn Pro Thr Ile Asp Leu Glu Asn Ser Tyr
```

```
                20              25              30
Val Pro Leu Gln Asn Gln Tyr Lys Asp Ile Arg Val Asp Glu His Pro
         35                  40                  45

Glu Tyr Leu His Asp Lys Glu Trp Ala Gln Ala Thr Tyr Asn Gly Asp
     50                  55                  60

Leu Val Gly Ile Lys Thr Ser Asp Val Met Leu Gly Val Tyr Val Pro
 65                  70                  75                  80

Lys Glu Glu Asp Val Gly Leu Gly Met Glu Leu Gly Tyr Ala Met Ser
                 85                  90                  95

Gln Gly Lys Tyr Val Leu Leu Val Ile Pro Asp Glu Leu Tyr Gly Glu
            100                 105                 110

Ser Ile Asn Leu Met Ser Trp Gly Val Ala Asp Asn Val Ile Lys Met
        115                 120                 125

Ser Glu Leu Ala Thr Phe Asp Phe Asn Arg Pro Arg Tyr Asn Phe Tyr
    130                 135                 140

Asp Gly Ala Val Tyr
145

<210> SEQ ID NO 28
<211> LENGTH: 157
<212> TYPE: PRT
<213> ORGANISM: Lactobacillus leichmannii

<400> SEQUENCE: 28

Met Pro Lys Lys Thr Ile Tyr Phe Gly Ala Gly Trp Phe Thr Asp Arg
 1               5                  10                  15

Gln Asn Lys Ala Tyr Lys Glu Ala Met Glu Ala Leu Lys Glu Asn Pro
                20                  25                  30

Thr Ile Asp Leu Glu Asn Ser Tyr Val Pro Leu Asp Asn Gln Tyr Lys
            35                  40                  45

Gly Ile Arg Val Asp Glu His Pro Glu Tyr Leu His Asp Lys Val Trp
        50                  55                  60

Ala Thr Ala Thr Tyr Asn Asn Asp Leu Asn Gly Ile Lys Thr Asn Asp
 65                  70                  75                  80

Ile Met Leu Gly Val Tyr Ile Pro Asp Glu Glu Asp Val Gly Leu Gly
                 85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Asn Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155

<210> SEQ ID NO 29
<211> LENGTH: 168
<212> TYPE: PRT
<213> ORGANISM: Lactobacillus fermentum

<400> SEQUENCE: 29

Leu Lys Asn Thr Asp Pro Val Ala Asn Thr Lys Ile Tyr Leu Ala Thr
 1               5                  10                  15

Ser Phe Phe Asn Glu Glu Gln Arg Ala Arg Ile Pro Gln Ala Leu Ala
                20                  25                  30

Gln Leu Glu Ala Asn Pro Thr Val Gly Val Val His Gln Pro Phe Asp
```

-continued

```
                35                  40                  45
Phe Gln Tyr Lys Asp Ala Arg Val Asp Ser Asp Pro Ala Gly Val Phe
             50                  55                  60

Gly Ser Leu Glu Trp Gln Ile Ala Thr Tyr Asn Asn Asp Leu Asn Ala
 65                  70                  75                  80

Val Gly Thr Ser Asp Val Cys Val Ala Leu Tyr Asp Met Asp Gln Ile
                 85                  90                  95

Asp Glu Gly Ile Cys Met Glu Ile Gly Met Phe Val Ala Leu His Lys
            100                 105                 110

Pro Ile Val Leu Leu Pro Phe Thr Lys Lys Asp Lys Ser Ala Tyr Glu
        115                 120                 125

Ala Asn Leu Met Leu Ala Arg Gly Val Thr Thr Trp Leu Glu Pro Asn
    130                 135                 140

Asp Phe Ser Pro Leu Lys Asp Phe Asn Phe Asn His Pro Met Ala Gln
145                 150                 155                 160

Pro Phe Pro Pro Phe Lys Val Phe
                165

<210> SEQ ID NO 30
<211> LENGTH: 167
<212> TYPE: PRT
<213> ORGANISM: Lactobacillus helveticus

<400> SEQUENCE: 30

Met Lys Ala Val Val Pro Thr Gly Lys Ile Tyr Leu Gly Ser Pro Phe
  1               5                  10                  15

Tyr Ser Asp Ala Gln Arg Glu Arg Ala Ala Lys Ala Lys Glu Leu Leu
             20                  25                  30

Ala Lys Asn Leu Ser Ile Ala His Val Phe Phe Pro Phe Asp Asp Gly
         35                  40                  45

Phe Thr Asp Pro Asp Glu Lys Asn Pro Glu Ile Gly Gly Ile Arg Ser
     50                  55                  60

Met Val Trp Arg Asp Ala Thr Tyr Gln Asn Asp Leu Thr Gly Ile Ser
 65                  70                  75                  80

Asn Ala Thr Cys Gly Val Phe Leu Tyr Asp Met Asp Gln Leu Asp Asp
                 85                  90                  95

Gly Ser Ala Phe Glu Ile Gly Phe Met Arg Ala Met His Lys Pro Val
            100                 105                 110

Ile Leu Val Pro Phe Thr Glu His Pro Glu Lys Glu Lys Lys Met Asn
        115                 120                 125

Leu Met Ile Ala Gln Gly Val Thr Thr Ile Ile Asp Gly Asn Thr Glu
    130                 135                 140

Phe Glu Lys Leu Ala Asp Tyr Asn Phe Asn Glu Cys Pro Phe Asn Pro
145                 150                 155                 160

Val Arg Gly Tyr Gly Ile Tyr
                165

<210> SEQ ID NO 31
<211> LENGTH: 146
<212> TYPE: PRT
<213> ORGANISM: Leuconostoc mesenteroides

<400> SEQUENCE: 31

Met Ser Gln Ile Tyr Leu Ala Gly Pro Phe Phe Ser Asp Glu Gln Ile
  1               5                  10                  15

Asp Arg Val Lys Arg Ile Glu Ala Ala Leu Asp Ser Asn Pro Thr Val
```

```
                    20                  25                  30
Thr Asp Tyr Tyr Ser Pro Arg Lys His Gln Lys Thr Glu Asn Pro Glu
                35                  40                  45

Phe Thr Ser Pro Trp Ala Ala Glu Val Phe Gln Arg Asp Ile Lys Asn
         50                  55                  60

Val Thr Asp Ala Asp Ile Ile Leu Ser Ile Ile Asp Tyr Arg Asp Asn
 65                  70                  75                  80

Asp Ala Asp Ser Gly Thr Ala Phe Glu Gln Gly Met Ala Trp Val Gln
                85                  90                  95

Lys Lys Pro Ile Ile Val Phe Asn Glu Leu Lys Phe Pro Val Asn Leu
            100                 105                 110

Met Leu Ser Glu Ser Leu Thr Ala Tyr Ile Thr Asn Ser Asp Asp Ile
            115                 120                 125

Ala Thr Tyr Asp Phe Asp Gln Thr Pro Lys Leu Pro Phe Thr Gly Glu
130                 135                 140

Leu Phe
145

<210> SEQ ID NO 32
<211> LENGTH: 154
<212> TYPE: PRT
<213> ORGANISM: Prochlorococcus marinus

<400> SEQUENCE: 32

Met Thr Arg Lys Ile Ile Tyr Leu Ala Ser Pro Tyr Gly Phe Ser Lys
  1               5                  10                  15

Gln Cys Lys Lys Asn Leu Leu Pro Glu Phe Ile Ala Ala Leu Glu Asp
             20                  25                  30

Leu Gly Ala Glu Val Trp Glu Pro Phe Ser Arg Asn Ala Gln Tyr Glu
         35                  40                  45

Asn Leu Gln Pro Gly Trp Ala His Asp Ile Ala Leu Ala Asp Leu Arg
     50                  55                  60

Asp Val Arg Asn Ser Asp Gly Ile Leu Ala Val Val Asn Gly Thr Pro
 65                  70                  75                  80

Pro Asp Glu Gly Val Met Ile Glu Leu Gly Ala Ala Ile Ala Leu Gly
                85                  90                  95

Lys Pro Thr Phe Leu Phe Arg Asp Phe Arg Arg Cys Ser Asp Ser
            100                 105                 110

Glu Glu Tyr Pro Leu Asn Leu Met Leu Phe Ala Gly Leu Pro Ser Ile
            115                 120                 125

Gly Trp Asn Asp Tyr Phe Tyr Thr Ser Ile Glu Glu Leu Ser Asp Pro
130                 135                 140

Lys Lys Ser Leu Ala Ile Trp Leu Lys Asp
145                 150
```